United States Patent
Takahashi et al.

(10) Patent No.: US 9,389,240 B2
(45) Date of Patent: Jul. 12, 2016

(54) AUTOMATIC ANALYZER

(75) Inventors: Kenichi Takahashi, Tokyo (JP); Isao Yamazaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/238,205

(22) PCT Filed: Jul. 19, 2012

(86) PCT No.: PCT/JP2012/068385
§ 371 (c)(1),
(2), (4) Date: Feb. 28, 2014

(87) PCT Pub. No.: WO2013/035444
PCT Pub. Date: Mar. 14, 2013

(65) Prior Publication Data
US 2014/0193918 A1    Jul. 10, 2014

(30) Foreign Application Priority Data

Sep. 6, 2011    (JP) .................................. 2011-194356

(51) Int. Cl.
*G01N 35/10*    (2006.01)
*G01N 35/02*    (2006.01)
*G01N 35/04*    (2006.01)

(52) U.S. Cl.
CPC ........ *G01N 35/1011* (2013.01); *G01N 35/1016* (2013.01); *G01N 35/025* (2013.01); *G01N 2035/0441* (2013.01); *G01N 2035/0443* (2013.01); *G01N 2035/1025* (2013.01); *Y10T 436/115831* (2015.01)

(58) Field of Classification Search
CPC ............. Y10T 436/119163; Y10T 436/11; Y10T 436/00; G01N 35/116; G01N 35/1011; G01N 35/1002; G01N 35/1009; G01N 35/10; G01N 2035/1018; G01N 2035/1062; G01N 2035/1048; G01N 2035/1027

USPC .................. 436/50, 43; 422/81, 68.1, 50
See application file for complete search history.

(56) References Cited

U.S. PATENT DOCUMENTS

2004/0034479 A1*  2/2004  Shimase et al. ................. 702/19

FOREIGN PATENT DOCUMENTS

| EP | 0 506 022 A2 | 9/1992 |
|---|---|---|
| JP | 01-167670 A | 7/1989 |
| JP | 06-003363 A | 1/1994 |
| JP | 2001-004641 A | 1/2001 |
| JP | 2005-227102 A | 8/2005 |
| JP | 2008-122333 A | 5/2008 |

OTHER PUBLICATIONS

International Preliminary Report on Patentability received in International Application No. PCT/JP2012/068385 dated Mar. 20, 2014.
European Patent Office; Supplementary European Search report mailed Mar. 10, 2015 in European patent application No. 12892330.5; 8 pages.

* cited by examiner

*Primary Examiner* — Christine T Mui
(74) *Attorney, Agent, or Firm* — Mattingly & Malur, PC

(57) ABSTRACT

An automatic analyzer adapted to enhance sample/reagent dispensing accuracy, regardless of a difference in sample/reagent dispensing height of a dispensing probe. When the amount of sample in a sample container is small, tip height "h1" of a sample dispensing probe positioned immediately after it has aspirated the sample decreases below tip height "h" of the sample dispensing probe positioned immediately before it discharges the sample. The sample in this state takes a concave shape at the tip of the sample dispensing probe positioned immediately before it discharges the sample. When the amount of sample in a sample container is large, tip height "h2" of the sample dispensing probe positioned immediately after it has aspirated the sample increases above the tip height "h'" and the sample takes a convex shape at the tip of the sample dispensing probe positioned immediately before it discharges the sample.

17 Claims, 9 Drawing Sheets

FIG. 9

ANALYTICAL PARAMETERS FOR TP ITEM

| AMOUNT OF SAMPLE | 2 μL |
|---|---|
| AMOUNT OF FIRST REAGENT | 180 μL |

CALIBRATION RESULTS FOR TP ITEM

| SAMPLE-ASPIRATING HEIGHT (mm) OF SAMPLE DISPENSING PROBE FROM SAMPLE DISK BOTTOM 12b | ENTERED CONCENTRATION VALUE OF THE STANDARD SOLUTION |
|---|---|
| 50mm | 6.00g/L |

STANDARD SOLUTION MEASUREMENT RESULTS FOR TP ITEM

| SAMPLE-ASPIRATING HEIGHT (mm) OF SAMPLE DISPENSING PROBE FROM SAMPLE DISK BOTTOM 12b | MEASURED CONCENTRATION VALUE OF THE STANDARD SOLUTION |
|---|---|
| 10mm | 5.88g/L |
| 90mm | 6.12g/L |

CORRECTION DATA CALCULATION EXPRESSIONS DERIVED FROM ASPIRATION HEIGHTS AND MEASURED VALUE $Y = -0.0005X + 1.0254$ $Z = (SAMPLE\ DISCHARGE\ QUANTITY * Y) - SAMPLE\ DISCHARGE\ QUANTITY$

X: SAMPLE DISPENSING PROBE HEIGHT FROM THE SAMPLE DISK BOTTOM
Y: CORRECTION COEFFICIENT
Z: THE AMOUNT OF CORRECTION (μL)

EXAMPLES OF DATA MEASURED AFTER TP ITEM CORRECTION WITH CORRECTION EXPRESSIONS

| VALUE MEASURED WITH TP ITEM MEASUREMENT STANDARD SOLUTION USED AS SAMPLE (g/L) EXPECTED VALUE: 6.00 g/L | TP ITEM MEASUREMENT SAMPLE-ASPIRATING HEIGHT OF SAMPLE DISPENSING PROBE FROM SAMPLE DISK BOTTOM 12b (mm) | CORRECTION COEFFICIENT CALCULATED FROM CORRECTION EXPRESSION | TP CONCENTRATION VALUE MEASURED AFTER CORRECTION USING THE CALCULATED AMOUNT OF CORRECTION (g/L) |
|---|---|---|---|
| 5.85 | 0 | 1.0254 | 6.00 |
| 5.88 | 10 | 1.0204 | 6.00 |
| 5.91 | 20 | 1.0154 | 6.00 |
| 5.94 | 30 | 1.0104 | 6.00 |
| 5.97 | 40 | 1.0054 | 6.00 |
| 6.00 | 50 | 1.0004 | 6.00 |
| 6.03 | 60 | 0.9954 | 6.00 |
| 6.06 | 70 | 0.9904 | 6.00 |
| 6.09 | 80 | 0.9854 | 6.00 |
| 6.12 | 90 | 0.9804 | 6.00 |
| 6.15 | 100 | 0.9754 | 6.00 |

FIG. 10

ANALYTICAL PARAMETERS FOR GLU ITEM

| AMOUNT OF SAMPLE | 3 μL |
|---|---|
| AMOUNT OF FIRST REAGENT | 150 μL |
| AMOUNT OF FIRST REAGENT | 500 μL |
| CONCENTRATION OF STANDARD SOLUTION | 300mg/dL |

CORRECTION DATA CALCULATION EXPRESSIONS DERIVED FROM THE SAMPLE DISCHARGE QUANTITY RATIO BY USING THE MEASUREMENT RESULTS FOR THE CALCULATION OF THE AMOUNT OF CORRECTION FOR THE TP ITEM (SAMPLE DISPENSING QUANTITY: 2 μL) AND CONVERTING THE MEASUREMENT RESULTS INTO THOSE TO BE APPLIED TO A SAMPLE DISCHARGE QUANTITY OF 3 μL $Y = -0.00033X + 1.0168$
$Z = $ (SAMPLE DISCHARGE QUANTITY $*$ Y) − SAMPLE DISCHARGE QUANTITY
X: SAMPLE DISPENSING PROBE HEIGHT FROM THE SAMPLE DISK BOTTOM
Y: CORRECTION COEFFICIENT
Z: THE AMOUNT OF CORRECTION (μL)

EXAMPLES OF DATA MEASURED AFTER GLU ITEM CORRECTION WITH CORRECTION EXPRESSIONS (SAMPLE DISPENSING QUANTITY: 3 μL)

| VALUE MEASURED WITH GLU ITEM MEASUREMENT STANDARD SOLUTION USED AS SAMPLE (mg/dL) EXPECTED VALUE: 300 mg/dL | GLU ITEM MEASUREMENT SAMPLE-ASPIRATING HEIGHT OF SAMPLE DISPENSING PROBE FROM SAMPLE DISK BOTTOM 12b (mm) | CORRECTION COEFFICIENT CALCULATED FROM CORRECTION EXPRESSION | GLU CONCENTRATION VALUE MEASURED AFTER CORRECTION USING THE CALCULATED AMOUNT OF CORRECTION (mg/dL) |
|---|---|---|---|
| 295 | 0 | 1.0168 | 3.00 |
| 296 | 10 | 1.0135 | 3.00 |
| 297 | 20 | 1.0102 | 3.00 |
| 298 | 30 | 1.0069 | 3.00 |
| 299 | 40 | 1.0036 | 3.00 |
| 300 | 50 | 1.0003 | 3.00 |
| 301 | 60 | 0.9970 | 3.00 |
| 302 | 70 | 0.9937 | 3.00 |
| 303 | 80 | 0.9904 | 3.00 |
| 304 | 90 | 0.9871 | 3.00 |
| 305 | 100 | 0.9838 | 3.00 |

FIG. 11

CORRECTION DATA SETTING SCREEN

| SELECT WHETHER TO EXECUTE CORRECTION | SAMPLE: EXECUTE | REAGENT: NOT EXECUTE |

THE AMOUNT OF SAMPLE CORRECTION: SET VALUE   EDIT

- HEIGHT 1 – DETECTION HEIGHT: 10 mm   ASPIRATION QUANTITY: +0.04 μL   DISCHARGE QUANTITY: +0.04 μL
- HEIGHT 2 – DETECTION HEIGHT: 40 mm   ASPIRATION QUANTITY: +0.01 μL   DISCHARGE QUANTITY: +0.01 μL
- HEIGHT 3 – DETECTION HEIGHT: 80 mm   ASPIRATION QUANTITY: −0.02 μL   DISCHARGE QUANTITY: −0.02 μL
- ...

THE AMOUNT OF SAMPLE CORRECTION: SET VALUE   EDIT

- HEIGHT 1 – DETECTION HEIGHT: 10 mm   ASPIRATION QUANTITY: +1.0 μL   DISCHARGE QUANTITY: +1.0 μL
- HEIGHT 2 – DETECTION HEIGHT: 30 mm   ASPIRATION QUANTITY: +0.5 μL   DISCHARGE QUANTITY: +0.5 μL
- HEIGHT 3 – DETECTION HEIGHT: 70 mm   ASPIRATION QUANTITY: −0.8 μL   DISCHARGE QUANTITY: −0.8 μL
- ...

FIG. 12

CORRECTION FUNCTION SETTING SCREEN

ITEM TO BE CORRECTED    TP

THE AMOUNT OF SAMPLE: 2 μL    :[EXECUTE CORRECTION]
THE AMOUNT OF REAGENT: 180 μL    :[NOT EXECUTE CORRECTION]
STANDARD SOLUTION-1 CONCENTRATION INPUT VALUE: 0.00 g/dL
STANDARD SOLUTION-2 CONCENTRATION INPUT VALUE: 6.00 g/dL
MEASURING HEIGHT    MEASURED CONCENTRATION OF STANDARD SOLUTION
HEIGHT 1: 10 mm    5.88 g/dL

HEIGHT 2: 90 mm    6.12 g/dL

CORRECTION DATA CALCULATION EXPRESSION
Y=-0.0005X+1.0254    EDIT

CORRECTION DATA CHECK:    ASPIRATION HEIGHT INPUT    : 0.04 μL    EDIT

AUTOMATIC ANALYZER

TECHNICAL FIELD

The present invention relates to an automatic analyzer that measures the concentration or activity value of a desired constituent contained in a multi-constituent sample such as blood or urine.

BACKGROUND ART

Automatic analyzers analyze the constituents of a substance such as blood and urine. Such an automatic analyzer includes a reaction cell that holds a reaction solution prepared by causing a reaction between a sample and a reagent, a sample dispensing probe that dispenses a predetermined amount of the reagent into the reaction cell from a sample container holding the sample, and a reagent dispensing probe that dispenses a predetermined amount of the reagent into the reaction cell from a reagent container holding the reagent. The analyzer causes the chemical reaction between the liquid sample and reagent dispensed from the sample dispensing probe and the reagent dispensing probe into the reaction cell, irradiating the resulting reaction solution with light from a halogen lamp or the like, measuring absorbance of the solution, and thus analyzing a constituent of the liquid sample.

In recent years, reduction in running costs of automatic analyzers by saving reagent consumption has been demanded. To meet this demand, the amount of sample dispensed is preferably decreased to lessen the amount of a reaction solution, while maintaining a ratio between the amount of sample and that of reagent. Accuracy in a trace amount of dispensing, therefore, is now an important factor in ensuring data reliability.

The dispensing probes for aspirating the sample and the reagent sense the liquid level with an aid of a liquid level sensing function, which is the technique described in Patent Document 1, for example, stop the immersion of the probe tip to a depth of a few or several millimeters in the sample or the reagent, and aspirate the sample or the reagent. The use of this sequence enables dispensing accuracy to be ensured by preventing an unnecessary amount of sample or reagent from being carried into or carried back from a reaction cell, and probe tip cleaning to be facilitated by ensuring an adequate sticking area of the sample or reagent on an outer wall of the probe.

PRIOR ART DOCUMENT

Patent Document

Patent Document 1: JP-2001-4641-A

SUMMARY OF THE INVENTION

Problems to be Solved by the Invention

When an automatic analyzer controls stopping operation of a downward movement of a dispensing probe which has sensed a liquid level in a sample or a reagent container, if the amount of sample or reagent in the container varies from container to container, height of the liquid level also differs, which in turn causes a difference in a stopping position of the dispensing probe according to container, hence causing a difference in aspiration height of the dispensing probe tip according to sample or reagent.

If the aspiration height of the dispensing probe tip differs according to sample or reagent, this causes pressure-associated differences in conditions relating to elastic deformation or the like of a fluid and a flow path, for example. The differences in these elastic deformation conditions lead to a difference in the quantity of air bubbles occurring at the dispensing probe tip immediately before it discharges the sample or reagent toward the reaction cell. Consequently the discharge quantity of the sample or reagent differs according to the particular container.

This causes a significant difference in the amount of sample or reagent discharge between, for example, a case that the sample or the reagent is aspirated from a deep position in the liquid level of the sample or reagent in the container because of a small amount of sample or reagent, and a case that the sample or the reagent is aspirated from a shallow position in the liquid level of the sample or reagent in the container because of a large amount of sample or reagent.

The difference in sample or reagent discharge quantity due to the difference in aspiration height has not been of a level that affects analysis with a conventional automatic analyzer. However, the tendency toward smaller amounts of dispensing in recent years makes such a difference an unignorably substantial error in a total amount of sample or reagent dispensed.

An example of conducting a measurement for an item relating to a total protein (TP) level in a sample whose discharge quantity is a trace amount as small as 2.00 microliters is described here. Suppose that when the stopping position of a sample dispensing probe tip as it aspirates a standard solution for calibration measurement is 50 mm above a bottom section of a sample disk, the discharge quantity of the standard solution from the sample dispensing probe, toward a reaction cell, is 2.00 microliters, which is equivalent to exactly 100% of a preset amount of 2.00 microliters.

Quality control sample measurement follows the calibration. During the measurement, when the stopping position of the sample dispensing probe tip as it aspirates the quality control sample is at a height of 10 mm below the bottom section of the sample disk, if the error in discharge quantity is −0.04 microliters, which is equivalent to 2% of 2.00 microliters, then a quality control value is 6.37 g/liter, which is 98% of an expected value of 6.50 g/liter, for example.

If the amount of sample discharged for TP measurement is 5.00 microliters, since the error of −0.04 microliters in discharge quantity is equivalent to 0.8% of 5.00 microliters, the quality control value includes an error of 6.45 g/liter, which is 99.2% of the expected value of 6.50 g/liter.

As discussed earlier herein, the error in a trace amount of dispensing is an important factor in determining whether data reliability can be obtained.

In the related art, however, no consideration is given to the fact that the differences in dispensing probe tip height with each sample/reagent dispensing cycle cause the changes in the discharge quantities of the sample or reagent. This in turn causes differences in measurement results, thus affecting measured-data reliability.

An object of the present invention is to provide an automatic analyzer and a liquid dispensing method adapted to solve the above problem and enhance sample/reagent dispensing accuracy, regardless of a difference in sample/reagent dispensing height of a dispensing probe.

Means for Solving the Problem

The present invention is configured as follows to attain the above object.

The invention includes a sample dispensing probe, a reagent dispensing probe, and an analyzing unit that analyzes a solution from the reaction of a sample with a reagent. The invention is constructed to detect a position where the sample dispensing probe or the reagent dispensing probe stops in the vertical position when the dispensing probe aspirates a predetermined amount of the sample or reagent from the sample container or the reagent container, and in accordance with the detected vertical stopping position, the amount of the sample or reagent to be aspirated/discharged into/from the sample or reagent dispensing probe may be corrected.

Effects of the Invention

The automatic analyzer and liquid dispensing method adapted to enhance sample/reagent dispensing accuracy, regardless of a difference in the sample/reagent dispensing height of the dispensing probe, can be provided.

BRIEF DESCRIPTION OF THE DRAWINGS

FIG. 9 is a diagram that shows an example of measurement based on a correction data calculation expression derived using the sample discharge quantity correction data calculation function in an embodiment of the present invention.

FIG. 10 is a diagram that shows an example of a measurement conducted after correction into an analytical item using the correction data calculation expression derived in an embodiment of the present invention.

FIG. 11 is a diagram that shows a correction data setting screen in an embodiment of the present invention.

FIG. 12 is a diagram that shows a correction function setting screen in an embodiment of the present invention.

FIG. 13 is a diagram that shows an analytical parameter setting screen in an embodiment of the present invention.

MODES FOR CARRYING OUT THE INVENTION

Hereunder, embodiments of the present invention will be described with reference to the accompanying drawings.

EMBODIMENTS

First Embodiment

Figure 1:
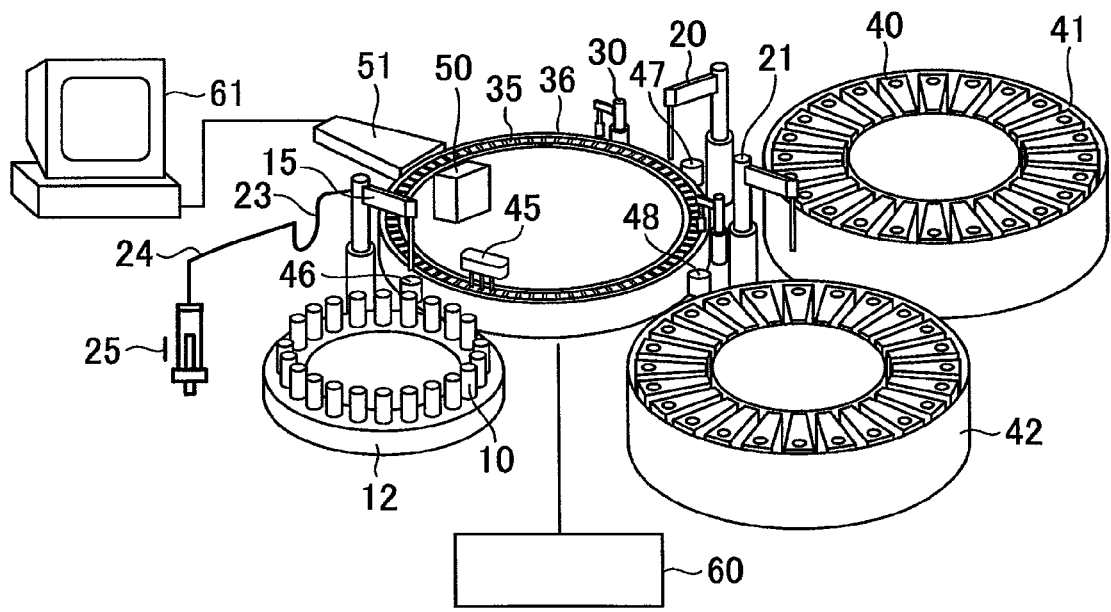
FIG. 1 is a schematic configuration diagram of an automatic analyzer applying the present invention.

FIG. 1 is a schematic configuration diagram of an automatic analyzer applying the present invention.

Referring to FIG. 1, the automatic analyzer includes a sample disk 12 constructed to have a plurality of sample containers 10 each for holding a sample, a first reagent disk 41 and a second reagent disk 42, both constructed to have a plurality of reagent containers 40 each for holding a reagent, and a reaction disk 36 with a plurality of reaction cells 35 arranged on a circumference of the disk 36.

The automatic analyzer also includes a sample dispensing mechanism 15 that dispenses into one of the reaction cells 35 the sample that has been aspirated from one of the sample containers 10, and a sample cleaning mechanism 46 that cleans the sample dispensing mechanism 15. The analyzer further includes a first reagent dispensing mechanism 20 that dispenses into the reaction cell 35 the reagent that has been aspirated from one of the reagent containers 40 in the first reagent disk 41, a first reagent cleaning mechanism 47 that cleans the first reagent dispensing mechanism 20, a second reagent dispensing mechanism 21 that dispenses into the reaction cell 35 the reagent that has been aspirated from one of the reagent containers 40 in the second reagent disk 42, and a second reagent cleaning mechanism 48 that cleans the second reagent dispensing mechanism 21. In addition, the analyzer includes a mixer 30 that mixes the liquids within the reaction cell 35, and a reaction cell cleaning mechanism 45 that cleans the reaction cell 35.

The automatic analyzer further includes a light source 50 placed near an outer circumference of the reaction disk 36, a spectroscopic detector 51, a computer 61 connected to the spectroscopic detector 51, and a controller 60 that controls operation of the entire analyzer and exchanges data with external apparatuses.

The sample dispensing mechanism 15 is connected to a fixed-volume dispensing syringe 25 via a flexible tube 23 and a fixed flow path 24.

Figure 2:
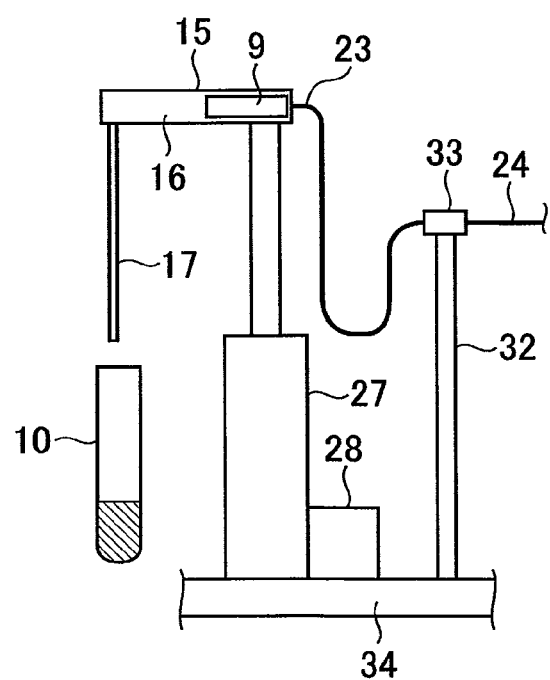
FIG. 2 is a configuration diagram of a sample dispensing mechanism.

FIG. 2 is a configuration diagram of the sample dispensing mechanism 15. The sample dispensing mechanism 15 in FIG. 2 includes a dispensing arm 16 that retains a sample dispensing probe 17 extending cylindrically in a vertical direction, a driving mechanism 27 set up on a base 34 to drive the dispensing arm 16 both vertically and in a rotational direction, and a motor 28 that operates the driving mechanism 27. The sample dispensing mechanism 15 also includes the flexible tube 23 connected to the sample dispensing probe 17. Additionally, the sample dispensing mechanism 15 includes a fixture 33 that retains one end of the flexible tube 23 and couples the end to the fixed flow path 24, and a support member 32 that retains the fixture 33.

The sample dispensing mechanism 15 further comes with a liquid level sensor 9. The liquid level sensor 9, for example, can sense a change in capacitance of the dispensing probe 17, thereby sensing the fact that the dispensing probe 17 has had its tip brought into contact with a liquid level of the sample in the sample container.

The first reagent dispensing mechanism 20 and the second reagent dispensing mechanism 21 also have substantially the same construction as that of the dispensing mechanism 15.

Operation of the automatic analyzer in the first embodiment of the present invention is described below.

Referring to FIG. 1, a sample to be examined, such as a blood sample, is placed in sample containers 10, the containers of which are then set up on the sample disk 12. The kinds of analyses to be conducted using the sample are entered by the controller 60. The sample that the sample dispensing mechanism 15 has picked is dispensed in given amounts into reaction cells 35 arranged on the reaction disk 36. Next, a given amount of reagent is dispensed from reagent containers 40 set up on the reagent disk 41 or 42, into the reaction cells 35 by the reagent dispensing mechanism 20 or 21, and the liquids in each of the reaction cells are mixed by the mixer 30.

The reaction disk 36 periodically repeats rotating and stopping, and the spectroscopic detector 51 conducts photometry in passage timing of each reaction cell 35 as it moves past in front of the light source 50. The photometry is repeated during a reaction time of 10 minutes, after which time, the reaction cell cleaning mechanism 45 drains a reaction solution from the reaction cell 35 and cleans the reaction cell. During these sessions, operation of other reaction cells 35 that uses another sample and another reagent is conducted concurrently.

The computer 61, which operates upon data that has been obtained during the photometry with the spectroscopic detector 51, calculates and displays concentrations of constituents corresponding to each kind of analysis. In addition, the computer 61 includes a screen display unit.

Next, operation of the sample dispensing mechanism 15 is described in detail below with reference to FIG. 2.

Referring to FIG. 2, before a sample is aspirated from a sample container 10, the fixed flow path 24 extending from the fixed-volume dispensing syringe 25 of FIG. 1 through the flow path and the flexible tube 23 to the sample dispensing probe 17 is filled with system water. Before the sample is aspirated, a trace amount of air is also aspirated as segmentation air into the tip of the sample dispensing probe 17.

The dispensing arm 16 moves downward by means of the driving mechanism 27 to insert the tip of the sample dispensing probe 17 into the sample contained in the sample container 10. At this time, the liquid level sensor 9 senses the liquid level of the sample. The tip of the sample dispensing probe 17 becomes immersed to a depth of several millimeters in the sample and stops moving. Then the fixed-volume dispensing syringe 25 aspirates a given amount of the sample into the sample dispensing probe 17.

After that, the driving mechanism 27 is operated to stop the dispensing probe 17 at its home position, whose height is greater than the height of upper ends of the sample container 10 and the reaction container 35, and which does not interfere with a rotating action of the dispensing arm 16. After upward movement of the dispensing probe 17 has been stopped, the dispensing arm 16 rotates by means of the driving mechanism 27 to move the sample dispensing probe 17 to a position above the reaction disk 36.

After that, the dispensing arm 16 moves downward by means of the driving mechanism 27 to insert the tip of the sample dispensing probe 17 into one reaction cell 35, whereby the fixed-volume dispensing syringe 25 is activated to discharge the sample from the dispensing probe 17 into the reaction cell 35. After a given amount of sample has been discharged into the reaction cell 35, the sample dispensing probe 17 moves upward and the sample cleaning mechanism 46 cleans the sample dispensing probe 17 to make this probe prepare for next analysis.

Figure 3:
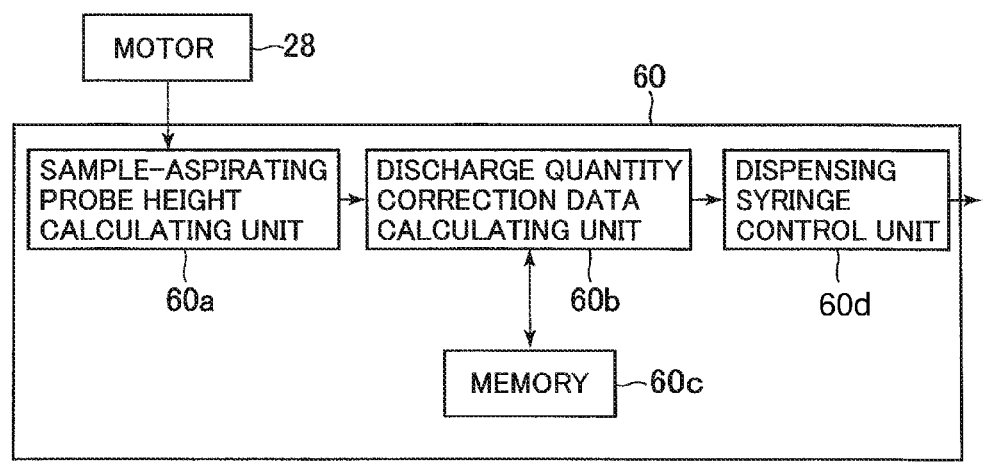
FIG. 3 is a configuration diagram that shows major internal function of a controller.

FIG. 3 is an internal function block diagram of the controller 60, showing major elements of the controller in the first embodiment of the present invention. The controller 60 in FIG. 3 includes a sample-aspirating probe height calculating unit 60a to which a pulse signal is supplied from the motor 28, and a memory 60c with internally prestored calculation expressions and more. The controller 60 also includes a discharge quantity correction data calculating unit 60b that calculates a discharge quantity correction value for the dispensing probe 17, based on height of the sample dispensing probe 17 that has been calculated by the sample-aspirating probe height calculating unit 60a, and on one of the calculation expressions prestored within the memory 60c. The controller 60 further includes a dispensing syringe operation control unit 60d that controls operation of the dispensing syringe in accordance with the discharge quantity correction value supplied from the discharge quantity correction data calculating unit 60b.

While the controller 60 also controls operation of the sample disk 12 and other sections of the automatic analyzer, function blocks relating to the operation control are omitted in FIG. 3.

Next, a relationship between the liquid level 37 of the sample in a sample container 10 and height of the liquid level 37 from a bottom section of the sample container 10 is described below with reference to FIG. 4.

Figure 4:
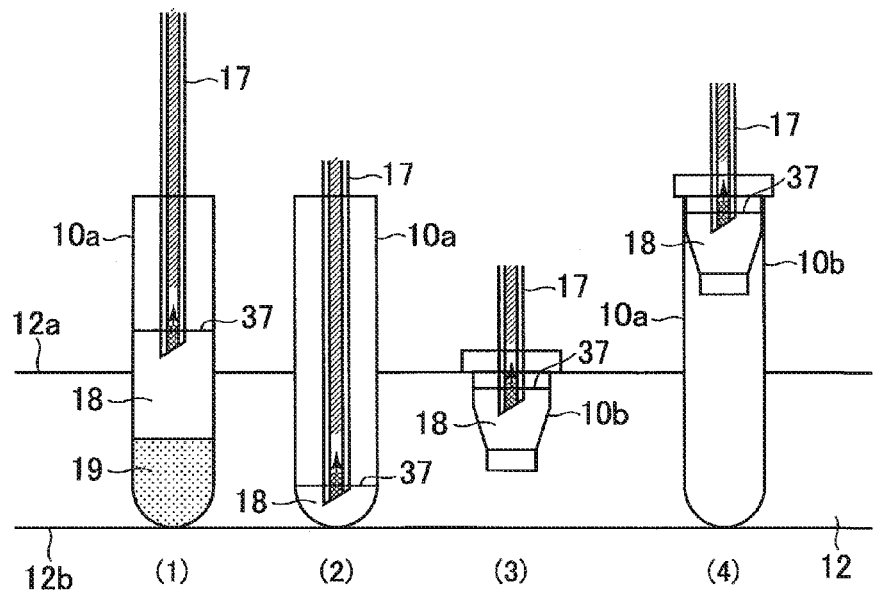
FIG. 4 is an explanatory diagram relating to an embodiment of the present invention, this diagram representing a relationship between a liquid level of a sample in a sample container and height of the liquid level from a bottom section of the sample container.

Referring to FIG. 4, sample containers 10 of several kinds in shape are usable. These include, for example, a test tube type of sample container 10a, which is set up with its lower end flush with a bottom section 12b of the sample disk 12, and a cup type of sample container 10b, which is set up with its neck flush with an upper surface 12a of the sample disk 12.

Condition (1) shown in FIG. 4 is next described below. For example, if the sample is blood, the sample container 10a is a vacuum tube for blood sampling. In this case, blood is sampled directly and after the blood has been separated into serum 18 and clot 19 by centrifuging, the sample container 10a is set up on the sample disk 12 and then the sample is aspirated by the sample dispensing probe 17.

At this time, the sample dispensing probe 17 uses a function of the liquid level sensor 9 to sense a liquid level of the serum 18 in the sample, and after immersing the tip of the probe to a depth of several millimeters in the sample-contained serum 18 and stopping the tip there, aspirates a necessary amount of the sample-contained serum 18 from that position.

In this way, under condition (1), the liquid level 37 of the sample in the sample container is positioned at a height equivalent to 30-80 mm above the sample disk bottom 12b.

Condition (2) falls under a case in which, for example, only a necessary amount of serum obtained by centrifuging is placed directly in the test tube type of sample container 10a. Under condition (2), since only the necessary amount of sample is placed in the container, the amount of sample in the container is small and a liquid level of the sample in the sample container is positioned at a height equivalent to 8-30 mm above the sample disk bottom 12b.

Condition (3) falls under a case in which, for example, only a necessary amount of serum obtained by centrifuging is likewise placed directly in the cup type of sample container 10b. Under condition (3), as under condition (2), only the necessary amount of sample is placed in the container and thus the amount of sample in the container is small, but since the sample container 10b itself is set up on the sample disk upper surface 12a, a liquid level of the sample in the sample container is positioned at a height equivalent to 30-50 mm above the sample disk bottom 12b.

Condition (4) applies to a case in which the sample container 10b is set up with the neck flush with an upper surface of the sample container 10a. This is the way in which the two sample containers are often used with a sample barcode, and the sample container 10a in this usage form is reused with the sample barcode attached thereto for sample identification only. The sample container 10b is therefore used as the sample container 10 actually containing the sample. Under condition (4), as under condition (2), only the necessary amount of sample is placed in the container and thus the amount of sample in the container is small, but since the sample container 10b itself is set up near the upper surface of the sample container 10a, a liquid level of the sample in the sample container is positioned at a height equivalent to 80-100 mm above the sample disk bottom 12b.

In this way, even when the same amount of sample is used for different kinds of sample containers or for some specific forms of analyzer operation, the height at which the sample dispensing probe 17 stops to aspirate the sample varies with the form of setting up the sample container 10.

Elastic deformation due to pressures exerted by the aspiration and discharge of the sample is described below.

Figure 5:
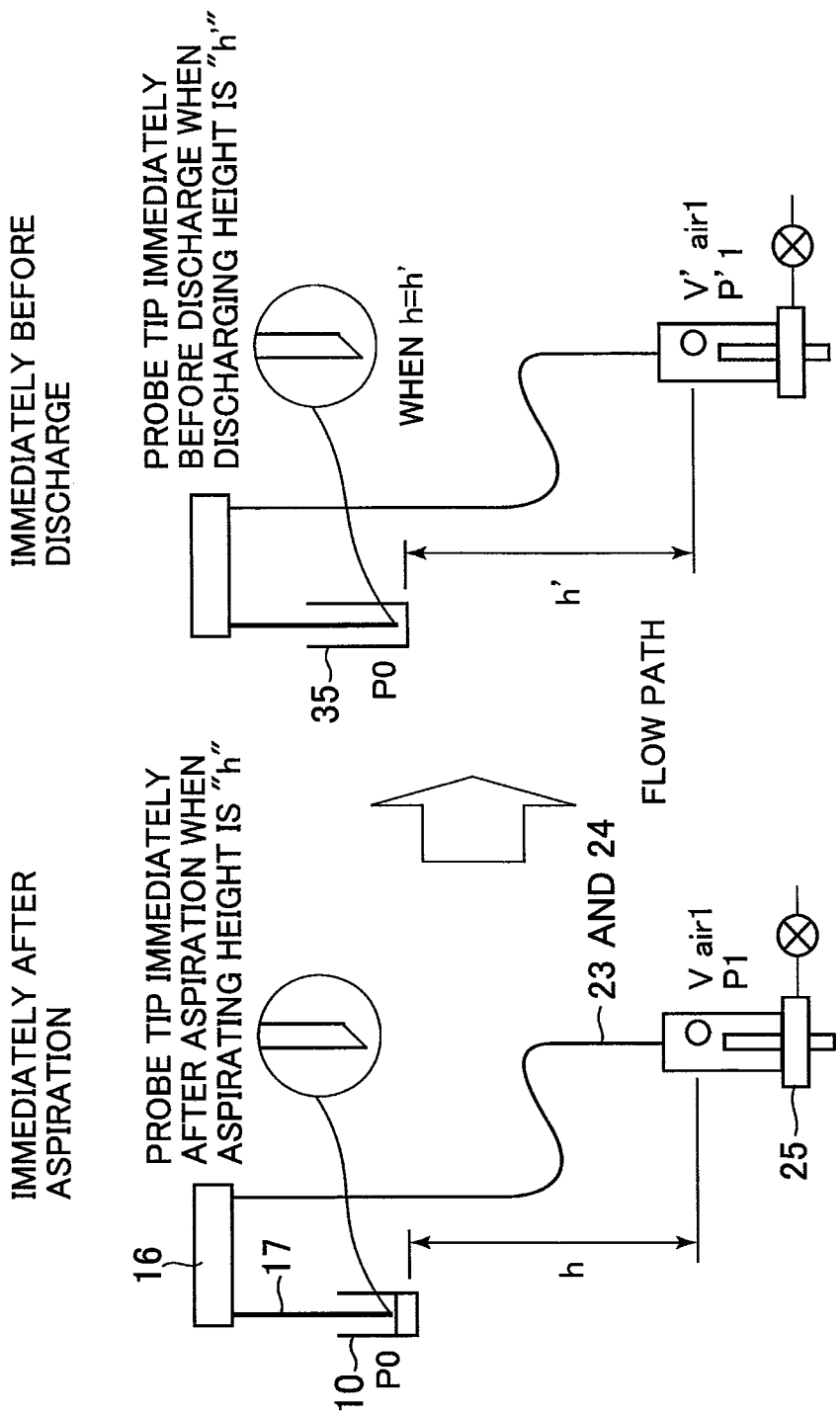
FIG. 5 is a diagram that shows geometric states of the sample at a sample dispensing probe tip positioned immediately after aspiration of the sample and immediately before discharge of the sample.

As shown in FIG. 5, the flow paths 23 and 24 from the fixed-volume dispensing syringe 25 to the sample dispensing probe 17 are filled with system water, and the flow paths are closed by a solenoid valve immediately before the sample is aspirated and immediately after it has been discharged. When the fixed-volume dispensing syringe 25 is driven to operate through a fixed stroke, therefore, the sample is aspirated (or discharged) from the tip of the sample dispensing probe 17 with the system water as a medium. For this reason, compression of the system water in the flow paths and the elastic deformation of the flow path members are continuously occurring in the system. Hereinafter, the amount of elastic deformation will be expressed in terms of equivalent air volume, and the air volume calculated will be handled as the equivalent air volume to mean the amount of elastic deformation.

A difference in a geometric state of the sample at the tip of the sample dispensing probe 17 due to a difference between the equivalent air volumes obtained immediately after the aspiration of the sample and immediately before the discharge of the sample is described below with reference to FIG. 5.

If the equivalent air volume obtained immediately after the sample has been aspirated is defined as Vair1, and the equivalent air volume obtained immediately before the sample is discharged is defined as V'air1, then the difference $\Delta$Vair between the equivalent air volume immediately after the aspiration of the sample and the equivalent air volume immediately before the discharge of the sample can be represented using the following expressions:

$$\Delta Vair = V'air1 - Vair1 \quad (1)$$

$$= -Vair1 \ (P'1 - P1)/P0 \quad (2)$$

$$= -Vair1 \ (h' - h)/h0 \quad (3)$$

$$= -Vair1 \ \Delta h/10 \quad (4)$$

where Vain is the equivalent air volume obtained immediately after the aspiration of the sample, V'air1 is the equivalent air volume obtained immediately before the discharge of the sample, and $\Delta$Vair is the difference between the equivalent air volume immediately after the aspiration of the sample and the equivalent air volume immediately before the discharge of the sample. In addition, P0 is an atmospheric pressure, P1 is a pressure existing immediately after the aspiration of the sample, and P'1 is a pressure existing immediately before the discharge of the sample. Furthermore, h0 is height of the water column balanced with the atmospheric pressure, "h" is height of the sample dispensing probe tip positioned immediately after the aspiration of the sample, and "h'" is height of the sample dispensing probe tip positioned immediately before the discharge of the sample. Moreover, $\Delta$h is a difference between the tip height of the sample dispensing probe 17 immediately after the aspiration of the sample and the tip height of the sample dispensing probe 17 immediately before the discharge of the sample.

As shown in FIG. 5, for example, when placement height of the fixed-volume dispensing syringe 25 fixed to the analyzer is taken as a perpendicular starting point, if the tip height "h" of the sample dispensing probe 17 positioned immediately after it has aspirated the sample is the same as the tip height "h'" of the sample dispensing probe 17 positioned immediately before it discharges the sample, it follows from expression (4) that $\Delta$Vair is 0 and hence that the geometric states of the sample at the tip of the sample dispensing probe 17 in both cases are the same.

Figure 6:
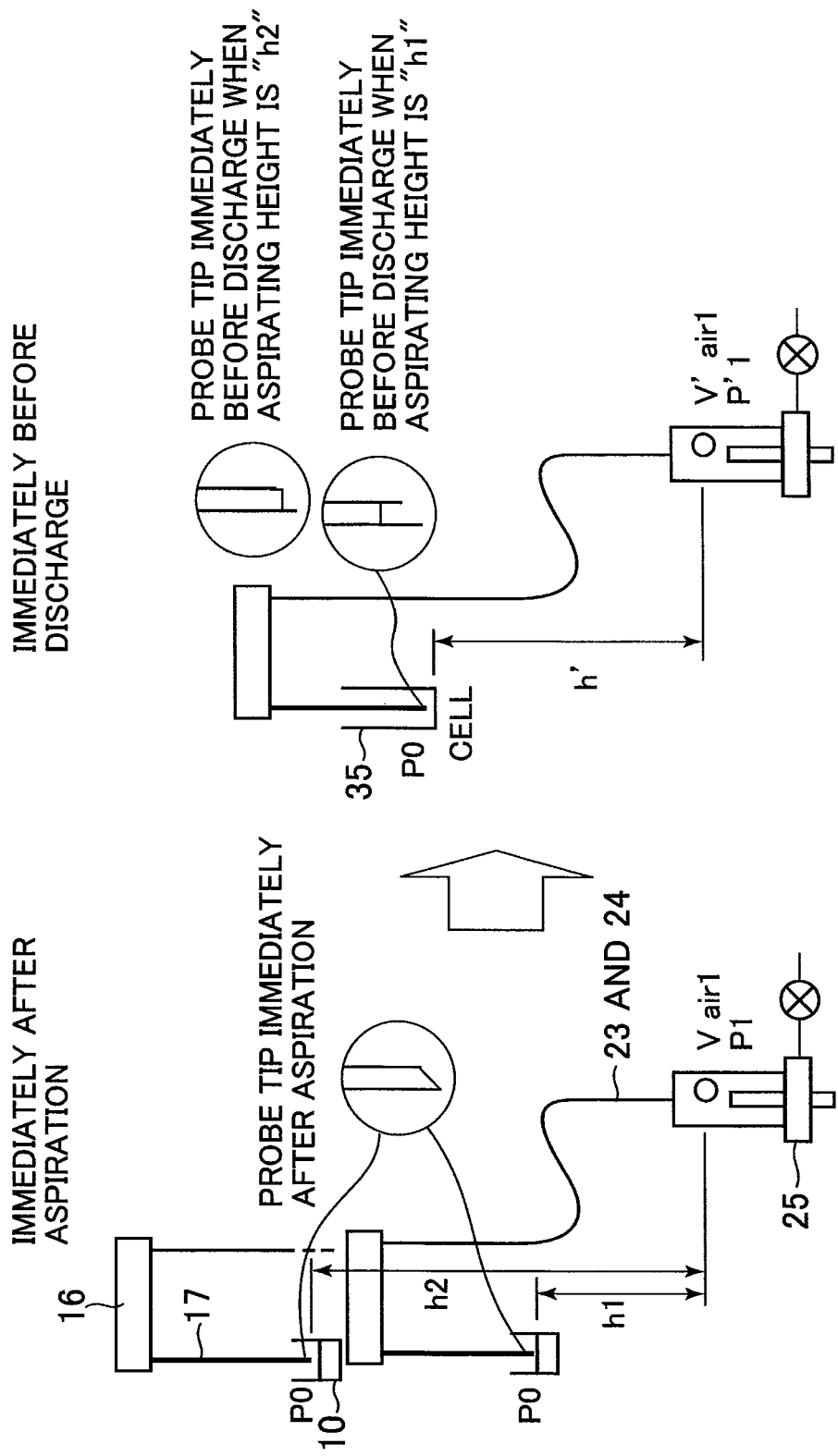
FIG. 6 is another diagram that shows geometric states of the sample at the sample dispensing probe tip positioned immediately after the aspiration of the sample and immediately before the discharge of the sample.

FIG. 6 is a diagram that shows an example in which the tip height of the sample dispensing probe 17 positioned immediately after it has aspirated the sample differs from the tip height of the sample dispensing probe 17 positioned immediately before it discharges the sample.

As shown in FIG. 6, for example as under condition (2) of FIG. 4, when the amount of sample in the sample container 10a is small, the tip height "h1" of the sample dispensing probe 17 positioned immediately after it has aspirated the sample decreases below the tip height "h'" of the sample dispensing probe 17 positioned immediately before it discharges the sample. It follows from expression (4), therefore, that the equivalent air volume $\Delta$Vair takes a minus value and hence that the sample takes a concave shape at the tip of the sample dispensing probe 17 positioned immediately before it discharges the sample.

Conversely when the amount of sample in the sample container is large, as under condition (4) of FIG. 4, the tip height "h2" of the sample dispensing probe 17 positioned immediately after it has aspirated the sample increases above the tip height "h'" of the sample dispensing probe 17 positioned immediately before it discharges the sample. It follows from expression (4), therefore, that the equivalent air volume $\Delta$Vair takes a plus value and hence that the sample takes a convex shape at the tip of the sample dispensing probe 17 positioned immediately before it discharges the sample.

As in the first embodiment of the present invention, when the sample-discharging tip height of the sample dispensing probe 17 is fixed at "h'" and the sample dispensing probe 17 uses the liquid level sensing function of the liquid level sensor 9 to detect the amount of sample in the sample container 10 and immerses the sample to the depth of several millimeters, the difference in the sample-aspirating tip height "h" of the sample dispensing probe 17 due to the difference in the liquid level of the sample in the sample container 10 appears as a difference in the discharge quantity of the sample.

For example, if the equivalent air volume Vain in the first embodiment of the present invention is 2.05 microliters, expression (5) can be derived from expression (4) as follows by calculating a difference d$\Delta$Vair existing between a differential equivalent air volume $\Delta$Vair' at a height of 8 mm in the liquid level of the sample in the sample container 10, above the sample disk bottom 12b, and a differential equivalent air volume $\Delta$Vair'' at a height of 100 mm:

$$d\Delta Vair = -2.05 \times 0.092/10 = -0.019 \text{ (microliters)} \quad (5)$$

where 0.092 is derived from 100 mm−8 mm=92 mm=0.092 m.

If the amount of sample dispensed is 1.50 microliters falling into a category of micro-volume dispensing, therefore, the difference of 0.019 microliters that was calculated using expression (5) appears as a discharge quantity error of about 1.3%.

Figure 7:
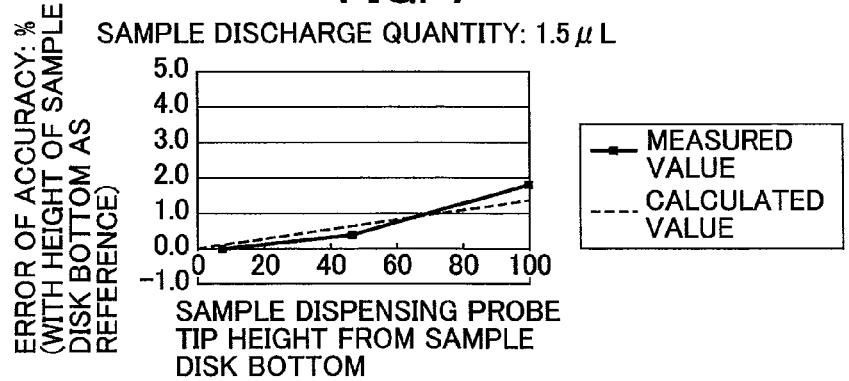
FIG. 7 is a graph that shows measurement results representing a relationship between measured data (shown with a solid line) and calculated data (shown with a dashed line), the measurements having been conducted for different aspiration heights of the sample.

FIG. 7 is a graph that shows measurement results representing a relationship between measured data (shown with a solid line) and calculated data (shown with a dashed line), the measurements having been conducted for different aspiration heights of the sample. As shown in FIG. 7, the measured data and the calculated data are substantially the same and associated expressions can be used to calculate correction data.

As can be seen from expression (4), the $\Delta V_{air}$ that has thus been calculated from the hardware configuration of the automatic analyzer is constant irrespective of the sample discharge quantity (i.e., the sample discharge quantity will be more influential as it becomes smaller).

Thus, $\Delta V_{air}$ can be calculated with the sample-aspirating tip height of the sample dispensing probe 17, and if this calculation result is corrected as the amount of fixed-volume dispensing syringe 25 driven to discharge the sample into the reaction cell 35, more accurate and more reliable data measurements can be performed.

In addition, since a concentration value of an analytical item (constituent) that is to be measured is determined by calibration results obtained on an analytical item basis, even more reliable data measurements can be performed if height of the sample dispensing probe tip positioned as it aspirates a standard solution for calibration measurement is adopted as sample-aspirating reference height of the sample dispensing probe 17.

The dispensing arm 16, driven by the motor 28, moves vertically when the sample-aspirating tip height of the sample dispensing probe 17 is detected. The sample-aspirating probe height calculating unit 60a calculates the number of strokes occurring during the vertical movement of the dispensing arm 16, from the number of pulses applied from the motor 28 at a stopping position of the arm upon the sensing of the liquid level.

Furthermore, the sample-discharging tip height "h'" of the sample dispensing probe 17, expression (4), and the amount of sample aspiration are stored within the memory 60c.

The correction data obtained by incorporating the above-described correction data calculation expressions can be used to correct the discharge quantity of the sample from the dispensing probe 17 by driving the dispensing syringe 17, therefore the difference in discharge quantity due to the difference in the sample-aspirating tip height of the dispensing probe can be eliminated.

As described above, in accordance with the first embodiment of the present invention, the error in sample discharge quantity, based on the difference between the sample-aspirating position and sample-discharging position of the sample dispensing probe, can be corrected by using the correction data calculated with the correction data calculation expressions. The automatic analyzer and liquid dispensing method adapted to enhance sample/reagent dispensing accuracy, regardless of the difference in the sample/reagent aspirating height of the dispensing probe, can be performed as a result.

Second Embodiment

The first embodiment of the present invention employs a method of calculating correction data by substituting an equivalent air volume for the amount of elastic deformation of the flow path members used to dispense the sample. The analyzer, however, may cause a difference in discharge quantity due to an influence of some other mechanism, such as flow path deformation other than the elastic deformation caused by vertical movements.

Accordingly a second embodiment of the present invention is configured to measure an independent discharge quantity for each different sample-aspirating height of the sample dispensing probe tip, then after applying to the analyzer software the error derived from the measured data, correct the amount of driving of the dispensing syringe, and thus remove the difference in discharge quantity.

In this case, the correction can likewise be conducted by providing, as a correction function, such a correction function screen as shown in FIG. 11 (i.e., a correction data setting screen, which is displayed on a screen display unit of the computer 61), entering the derived error value for the particular sample or reagent into the analyzer screen, and calculating the height-specific correction data based on the entered error value.

The above correction function also allows independent correction on an analyzer-by-analyzer basis, which in turn allows the function to be utilized for further enhancement of reliability. In addition, even when the flow paths need to be changed in hardware configuration, the correction data can be modified by merely entering modification data into the screen without introducing a change in the software. The enhancement of reliability and the modification of the correction data lead to enhancing convenience.

As shown in FIG. 11, the correction data setting screen is also provided with buttons that allow a user to select whether a correction is to be conducted for the amount of sample and the amount of reagent independently.

Furthermore, a practically acceptable error in discharge quantity may be calculated on an analyzer-specific basis and for each sample-aspirating height, and the calculation results themselves may be corrected. At this time, successive procedural operations for calculating the sample discharge quantity correction data may be automated and incorporated into the analyzer as a correction data calculating function for the sample discharge quantity.

The analyzer configuration in the second embodiment of the present invention is substantially the same as that of the first embodiment, so that illustration of the configuration is omitted.

Figure 8:
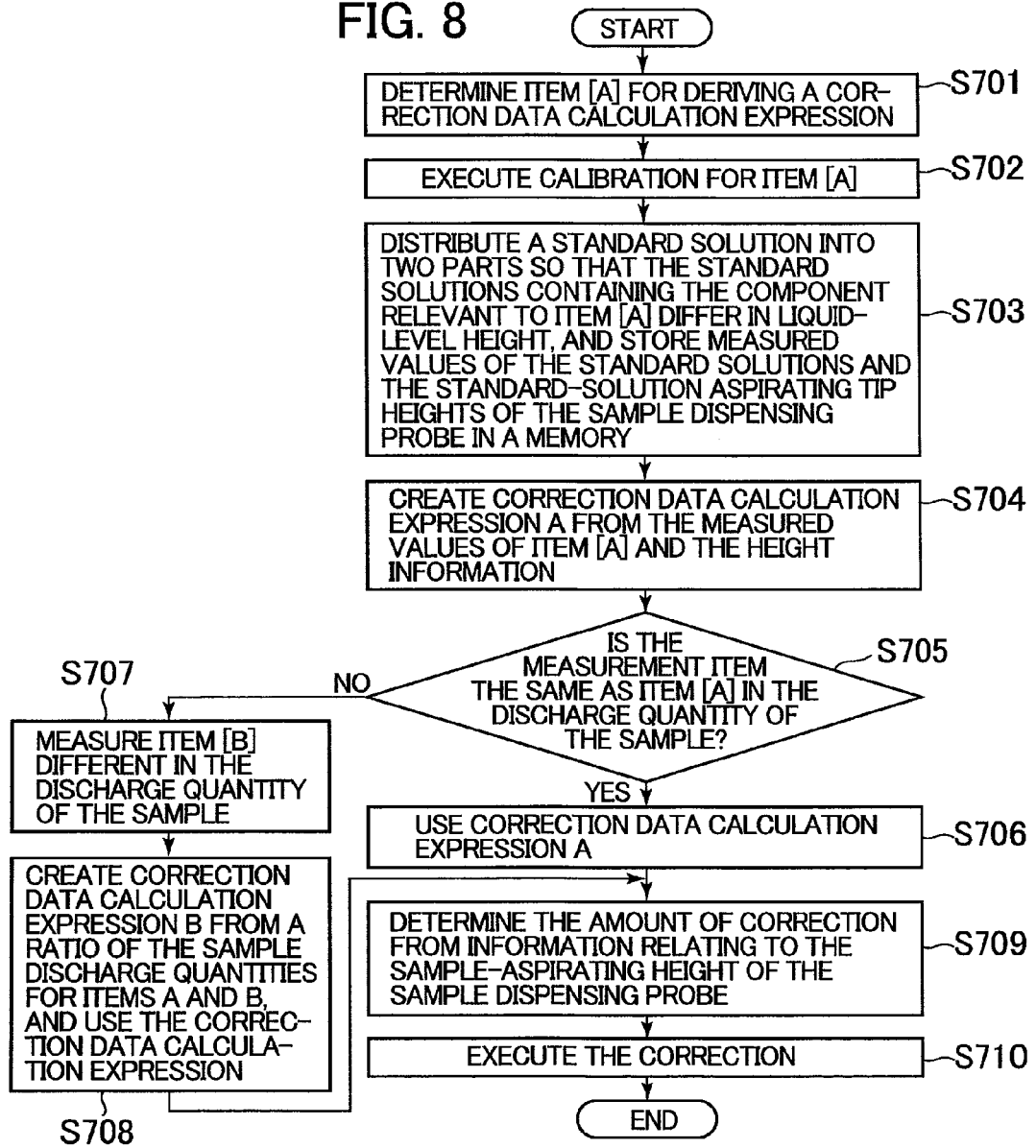
FIG. 8 is a flowchart of a sample discharge quantity correction data calculation function in a first embodiment of the present invention.

FIG. 8 is a flowchart of the sample discharge quantity correction data calculation function in the second embodiment of the present invention. FIG. 9 is a diagram that shows an example of a calculation conducted for the correction of the TP level in accordance with the flowchart shown in FIG. 8.

Item [A] for deriving the correction data calculation expression is first determined in FIG. 8. For example, a sample discharge quantity of 2.00 microliters and the TP item, which is a micro-volume dispensing item, are registered as items to be corrected (step S701).

Calibration for item [A], or in the present example, the TP item, is next executed. Tip height of the sample dispensing probe 17 as it aspirates a standard solution at this time, is registered in the memory 60c via the sample-aspirating probe height calculating unit 60a and the discharge quantity correction data calculating unit 60b(step S702).

Suppose, for example, that as indicated by TP item calibration results in FIG. 9, a standard solution concentration value of 6.00 g/L is entered and that the standard-solution aspirating tip height of the sample dispensing probe 17 from the sample disk bottom 12b is 50 mm.

Next, an actual concentration of the standard solution for the TP item is measured. Prior to the measurement, the standard solution is distributed into two parts and the containers containing the standard solutions are set up in the analyzer so that as under conditions (2) and (4) of FIG. 4, for example, the liquid-level heights of the standard solutions from the sample disk bottom 12b differ, and actual concentrations of the standard solutions are measured. The standard-solution aspirating tip heights of the sample dispensing probe 17 at this time are registered in the memory 60c (step S703).

Suppose, for example, that as indicated by the standard-solution measurement results shown in FIG. 9 for the TP item, the concentration value that has been measured when the standard solution was aspirated under condition (2) of FIG. 4 is 5.88 g/L, which is 98% of the entered concentration value of 6.00 g/L of the standard solution, and that the standard-solution aspirating tip height of the sample dispensing probe 17 at that time was 10 mm from the sample disk bottom 12b.

On the other hand, suppose that the concentration value that has been measured when the standard solution was aspirated under condition (4) of FIG. 4 is 6.12 g/L, which is 102% of the entered concentration value of 6.00 g/L of the standard solution, and that the standard-solution aspirating tip height of the sample dispensing probe 17 at that time was 90 mm from the sample disk bottom 12b.

Correction data calculation expressions are created from the concentration values and aspirating heights obtained during the measurement of the two standard solutions (step S704). The as-calibrated TP standard solution aspirating height calculated in steps S702 and S703 was taken as reference height when the above concentration values and aspirating heights were measured.

For example, expressions (6) and (7) are the correction data calculation expressions for the TP item in FIG. 9.

$$Y=-0.0005X+1.0254 \quad (6)$$

$$Z=(\text{Sample discharge quantity}) \times Y-(\text{Sample discharge quantity}) \quad (7)$$

where X denotes the tip height of the sample dispensing probe 17 from the sample disk bottom 12b, Y denotes a correction coefficient, and Z denotes the amount of correction (in microliters).

It can be confirmed that as shown in FIG. 9, a measured value of 6.00 g/L, an expected value, can be obtained if the concentration of the TP item standard solution that was measured for each sample-aspirating tip height of the sample dispensing probe 17 is corrected using expression (6).

FIG. 12 is a diagram that shows the setting screen for the above-described correction function, and the user can use this setting screen to select an item to be corrected, select whether to execute the quantitative correction of the sample and the reagent independently, and edit and confirm the concentration and the height by entering the respective correction data calculation expressions and correction values. This screen is displayed on the screen display unit of the computer 61.

As described above, from expression (4), the differential equivalent air volume ΔVair is constant irrespective of the magnitude of the sample discharge quantity, so the correction data calculation expression to be obtained is the same if the sample discharge quantities are the same.

Since the amount of sample discharged for the correction of the TP level is 2.00 microliters, 98% of this value amounts to 1.96 microliters, derived by subtracting the error of −0.04 microliters due to the difference in tip height, and 102% of 2.00 microliters amounts to 2.04 microliters, derived by adding an error of 0.04 microliters due to the difference in tip height.

In contrast with the above, if the discharge quantity of the sample is 3.00 microliters, 2.96 microliters at the error of −0.04 microliters is equivalent to 98.7% and 3.04 microliters at an error of +0.04 microliters is equivalent to 101.3%.

Using the ratio of the sample discharge quantities from these relationships allows expression (6), which is the correction data calculation expression for the TP item, to be rewritten for application to a different item relating to the sample discharge quantity. FIG. 10, for example, shows an example of a correction data calculation expression derived by using the TP item measurement results of FIG. 9 and rewriting expression (6) so that this expression can be applied to a GLU item involving the sample discharge quantity of 3.00 microliters.

As shown in FIG. 10, the following is the correction data calculation expression for the sample discharge quantity of 3.00 microliters:

$$Y=-0.00033X+1.0168 \quad (8)$$

It can be confirmed that as shown in FIG. 10, for example, a measured value of 300 mg/dL, an expected value, can be obtained if a concentration value of the GLU item that was measured for each sample-aspirating tip height of the sample dispensing probe 17 is corrected using expression (8).

As described above, the second embodiment of the present invention uses a TP item to derive a correction data calculation expression. If a correction data calculation expression for a single item is found, however, this correction data calculation expression can also be used as a basis to derive correction data calculation expressions for all other items by performing arithmetic operations according to the particular ratio of the sample discharge quantities.

It is therefore checked whether the sample discharge quantity for the item whose concentration is to be measured is the same as that of item [A] for which the correction data calculation expression has been derived.

In the second embodiment of the present invention, it is checked in step S705 whether the sample discharge quantity for the item whose concentration is to be measured is the same as the sample discharge quantity of 2.00 microliters for the TP item. If in step S705 the sample discharge quantity for the measurement item is found to be 2.00 microliters, expression (6) is used as the correction data calculation expression for the measurement item (step S706). Next, the amount of correction is determined from the sample-aspirating tip height of the sample dispensing probe 17 for the measurement item (step S709). After this, for example, the amount of sample discharged via the dispensing syringe 25 is changed according to the amount of correction that has been determined, and the correction takes place (step S710).

If in step S705 the sample discharge quantity for the measurement item is different from that of item [A], a correction data calculation expression is derived from the amount of sample dispensed for the measurement item and the correction is conducted. In the second embodiment of the present invention, if the GLU item is selected as the measurement item (step S707), expression (7) based on expression (6) is derived from the ratio of the sample discharge quantities, in step S708, and the correction is conducted using expression (8).

In accordance with this operating flow diagram, a practically acceptable error in discharge quantity can be determined automatically for each automatic analyzer and each sample-aspirating height. The correcting function can also be applied to practically all analytical items different in sample discharge quantity. These features and characteristics of the present invention render it contributory to enhancing the reliability of data measurements.

In addition, a screen that allows the user to select whether to perform the correction of the discharge quantity may be prepared for the case that the user will hate using a different operating procedure for each measuring cycle, or that when there is a margin on a clinical tolerance of the measurement item, the user will judge the correction to be unnecessary.

Alternatively, as shown in FIG. 13, a screen for selecting the application of the correcting function only to items up to 3.00 microliters in quantity, for example, may be displayed on the screen display unit of the computer 61. The screen in FIG. 13 enables the user, for example, to select whether to perform independent corrections on an item-by-item basis when setting an analytical parameter for each item, or to apply the correcting function only to trace quantities of discharge that are significantly affected by the error in discharge quantity.

Further alternatively, for example, a screen for viewing a function relating to an automatic correction data calculation expression may be provided to enable completion of the successive operations shown in FIG. 8 and described in the example relating to the correction data calculation function for the sample discharge quantity. This screen may enable the user to select item [A] for finding the automatic correction data calculation expression, and to view measurement results, height information, and the correction data calculation expression. The screen may further enable the measurement results and the height information to be edited and hence the correction data calculation expression to be arithmetically derived once again or to be directly edited.

In the embodiments described above, the correction relating to the analyzer is by changing the amount of driving of the dispensing syringe, according to the particular amount of correction, and then directly correcting the sample discharge quantity itself. The sample discharge quantity, however, may not be corrected. Instead, for example, the computer 61, an analyzing unit, may be made to calculate the discharged sample or reagent quantity from a vertical position corresponding to the aspirating height of the sample or reagent, and correct the measured concentration value.

The correction can then be performed just by executing software-based arithmetic processing without changing hardware operation.

In addition, several kinds of methods are usable as sample dispensing schemes. For example, if the amount of sample needed for analysis is 2.00 microliters, sample dispensing may use a scheme in which the sample dispensing probe 17 aspirates a greater amount of sample than is needed for the analysis, and discharges only the amount of sample needed for the analysis.

Furthermore, if the amount of sample needed for analysis is less than 2.00 microliters, some analyzers use a sample dispensing scheme in which the sample dispensing probe 17 aspirates only the amount of sample needed for the analysis and discharges the aspirated sample by forcing it out with the system water.

The correction of the discharge quantity only has been described in the first and second embodiments of the present invention. If the amount of sample needed for the analysis is less than 2.00 microliters, however, the aspiration quantity may also be made correctable where its correction is determined to be necessary in a scheme such as using the system water to force the sample out.

Moreover, while the error in discharge quantity due to the difference in pressure in the sample-aspirating height direction of the sample dispensing probe 17 has been described in the present invention, since the error in discharge quantity is likely to be due to other reasons such as the influence of a change in volume due to the deformation of the flow paths, the correction may be conducted by calculating the appropriate amount of correction according to a particular difference in operation such as the rotational direction or horizontal direction of the sample dispensing probe 17.

In this case, the sample-aspirating probe height calculating unit 60$a$ shown in FIG. 3 will calculate a rotational angle or horizontal position of the sample dispensing probe 17 as well as the height of the probe.

While the sample discharge in which the error in discharge quantity significantly impacts a total discharge quantity has been described in the embodiments of the present invention above, the amount of reagent can be corrected even during the reagent discharge operation involving the same analyzer configuration, by executing substantially the same kind of processing as that of sample dispense operation. That is to say, the reagent discharge quantity can be corrected on the basis of a vertical position corresponding to height of a reagent dispensing probe existing as it aspirates the reagent from the reagent container 40 via the reagent dispensing mechanism 20 or 21. The reagent dispensing mechanism 20, 21 is substantially of the same configuration as that of the sample dispensing mechanism 15 shown in FIG. 2, and the sample dispensing probe 17 can function as the reagent dispensing probe.

For this reason, FIG. 2 can be used as a figure that shows the reagent dispensing mechanism 20, 21 and the sample dispensing mechanism 15.

When the discharge quantity from the reagent dispensing probe is corrected, sample-aspirating probe height calculating unit 60$a$ shown in FIG. 3 operates as a reagent-aspirating probe height calculating unit, the discharge quantity correction data calculating unit 60$b$ operates as a sample and reagent discharge quantity correction data calculating unit 60, and the dispensing syringe operation control unit 60$d$ operates as a sample and reagent dispensing syringe operation control unit.

DESCRIPTION OF REFERENCE CHARACTERS

9: Liquid level sensor
10: Sample container
10$a$: Test tube type of sample container
10$b$: Cup type of sample container
12: Sample disk
12$a$: Sample disk upper surface
12$b$: Sample disk bottom
15: Sample dispensing mechanism
16: Dispensing arm
17: Sample dispensing probe
18: Serum
19: Clot
20: First reagent dispensing mechanism
21: Second reagent dispensing mechanism
23: Flexible tube
24: Fixed flow path
25: Fixed-volume dispensing syringe
27: Driving mechanism
28: Motor
30: Mixer
32: Support member
33: Fixture
34: Base
35: Reaction cell
36: Reaction disk
37: Liquid level of sample
40: Reagent container
41: First reagent disk
42: Second reagent disk 45: Reaction cell cleaning mechanism
46: Sample cleaning mechanism
47: First reagent cleaning mechanism
48: Second reagent cleaning mechanism
50: Light source
51: Spectroscopic detector
60: Controller
60a: Sample-aspirating probe height calculating unit
60b: Discharge quantity correction data calculating unit
60c: Memory
60d: Dispensing syringe operation control unit
61: Computer

The invention claimed is:

1. An automatic analyzer comprising:
a sample dispensing probe that dispenses a sample into a reaction cell from a sample container holding the sample;
a sample dispensing syringe connected to the sample dispensing probe through a flexible tube;
a sample dispensing motor that drives the sample probe in a vertical direction;
a reagent dispensing probe that dispenses a reagent into the reaction cell from a reagent container holding the reagent;
a reagent dispensing syringe connected to the reagent dispensing probe through a flexible tube;
a reagent dispensing motor that drives the reagent dispensing probe in the vertical direction; and
an analyzing unit that analyzes a solution from the reaction of the sample with the reagent, wherein
the automatic analyzer further comprises a controller connected to each of the sample dispensing motor, reagent dispensing motor, sample dispensing syringe, and reagent dispensing syringe,
wherein the controller is programmed to:
based on signals from the sample dispensing motor or reagent dispensing motor, detect a first position where the sample dispensing probe or the reagent dispensing probe stops in the vertical direction from a predetermined reference point when the sample dispensing probe or the reagent dispensing probe aspirates a predetermined volume of the sample or reagent from the sample container or the reagent container,
based on signals from the sample dispensing motor or reagent dispensing motor, detect a second position where the sample dispensing probe or the reagent dispensing probe stops in the vertical direction from the predetermined reference point when the sample dispensing probe or the reagent dispensing probe discharges the sample or regent into the reaction cell,
determine a corrected discharge quantity value of the sample or the reagent based on a difference between the detected first position and the detected second position, and
control the operation of the sample dispensing syringe or the reagent dispensing syringe to discharge the sample or the reagent based on the corrected discharge quantity value.

2. An automatic analyzer comprising:
a sample dispensing probe that dispenses a sample into a reaction cell from a sample container holding the sample;
a sample dispensing syringe connected to the sample dispensing probe through a flexible tube;
a sample dispensing motor that drives the sample probe in a vertical direction;
a reagent dispensing probe that dispenses a reagent into the reaction cell from a reagent container holding the reagent;
a reagent dispensing syringe connected to the reagent dispensing probe through a flexible tube; and an analyzing unit that analyzes a solution from the reaction of the sample with the reagent; and
a reagent dispensing motor that drives the reagent dispensing probe in the vertical direction,
wherein the automatic analyzer further comprises a controller for controlling operation of the sample or reagent dispensing probe and is connected to each of the sample dispensing motor, reagent dispensing motor, sample dispensing syringe, and reagent dispensing syringe,
wherein the controller programmed to:
based on signals from the sample dispensing motor or reagent dispensing motor, detect a first position where the sample dispensing probe or reagent dispensing probe stops in the vertical direction from a predetermined reference point when the sample dispensing probe or the reagent dispensing probe aspirates a predetermined volume of the sample or reagent from the sample container or the reagent container,
based on signals from the sample dispensing motor or reagent dispensing motor, detect a second position where the sample dispensing probe or the reagent dispensing probe stops in the vertical direction from the predetermined reference point when the sample dispensing probe or the reagent dispensing probe discharges the sample or regent into the reaction cell,
determine a corrected discharge quantity value of the sample or reagent based on a difference between the first detected position and the detected second position,
control the operation of the sample dispensing syringe or the reagent dispensing syringe to discharge the sample or the reagent based on the corrected discharge quantity value, and
wherein the analyzing unit corrects measurement results output in association with each of the detected first position and the detected second position of the sample or reagent dispensing probe from the predetermined reference point.

3. The automatic analyzer according to claim 1, further comprising:
a screen display connected to the controller,
wherein the controller is further programmed to display respective volumes of aspiration or discharge of the sample or reagent in association with each of the detected first position and detected second position of the sample or reagent dispensing probe.

4. The automatic analyzer to claim 1, further comprising:
a screen display connected to the controller,
wherein the controller is further programmed to display a screen for selecting a measurement item, entering a correction amount with respect to the aspiration or discharge of the sample or reagent, and deriving a calculation expression for the correction amount.

5. The automatic analyzer according to claim 1, further comprising:
a screen display connected to the controller,
wherein the controller is further programmed to display a screen for selecting whether the correction, with respect to the aspiration or discharge of the sample or reagent, or to the measured data, will be applied to analytical items to be measured.

6. The automatic analyzer according to claim 1, further comprising:

a screen display connected to the controller, wherein the controller is further programmed to display a screen for selecting, on an analytical item basis, whether the correction, with respect to the aspiration or discharge of the sample or reagent, or to the measured data, will be applied.

7. A liquid dispensing method for use in an automatic analyzer including a sample dispensing probe that dispenses a sample into a reaction cell from a sample container holding the sample, a sample dispensing syringe connected to the sample dispensing probe through a flexible tube, a sample dispensing motor that drives the sample probe in a vertical direction, a reagent dispensing probe that dispenses a reagent into the reaction cell from a reagent container holding the reagent, a reagent dispensing syringe connected to the reagent dispensing probe through a flexible tube, a reagent dispensing motor that drives the reagent dispensing probe in the vertical direction, and an analyzing unit that analyzes a solution from the reaction of the sample with the reagent, the dispensing method comprising the steps of:

detecting a first position where the sample dispensing probe or the reagent dispensing probe stops in the vertical direction from a predetermined reference point when the sample dispensing probe or the reagent the dispensing probe aspirates a predetermined volume of the sample or reagent from the sample container or the reagent container;

detecting a second position where the sample dispensing probe or the reagent dispensing probe stops in the vertical direction from the predetermined reference point when the sample dispensing probe or the reagent dispensing probe discharges the sample or regent into the reaction cell;

determining a corrected discharge quantity value of the sample or reagent based on a difference between the detected first position and the detected second position; and controlling the operation of the sample dispensing syringe or the regent dispensing syringe to discharge the sample or the reagent based on the corrected discharge quantity value.

8. A liquid dispensing method for use in an automatic analyzer including a sample dispensing probe that dispenses a sample into a reaction cell from a sample container holding the sample, a sample dispensing syringe connected to the sample dispensing probe through a flexible tube, a sample dispensing motor that drives the sample probe in a vertical direction, a reagent dispensing probe that dispenses a reagent into the reaction cell from a reagent container holding the reagent, a reagent dispensing syringe connected to the reagent dispensing probe through a flexible tube, a reagent dispensing motor that drives the reagent dispensing probe in the vertical direction, and an analyzing unit that analyzes a solution from the reaction of the sample with the reagent, the dispensing method comprising the steps of:

controlling operation of the sample or reagent dispensing probe;

detecting a first position where the sample dispensing probe or reagent dispensing probe stops in the vertical direction from a predetermined reference point when the sample dispensing probe or the reagent dispensing probe aspirates a predetermined volume of the sample or reagent from the sample container or the reagent container;

detecting a second position where the sample dispensing probe or the reagent dispensing probe stops in the vertical direction from the predetermined reference point when the sample dispensing probe or the reagent dispensing probe discharges the sample or regent into the reaction cell;

determining a corrected discharge quantity value of the sample or reagent based on a difference between the detected first position and the detected second position;

controlling the operation of the sample dispensing syringe or the regent dispensing syringe to discharge the sample or the reagent based on the corrected discharge quantity value; and correcting measurement results output in association with each of the detected first position and detected second position of the sample or reagent dispensing probe from the predetermined reference point.

9. The liquid dispensing method for use in an automatic analyzer according to claim 7, further comprising:

displaying a screen displaying respective amounts with respect to the aspiration or discharge of the sample or reagent in association with each of the controller-detected vertical stopping positions of the sample or reagent dispensing probe.

10. The liquid dispensing method for use in an automatic analyzer according to claim 7, further comprising:

calculating a correction amount with respect to the aspiration or discharge of the sample or reagent in association with each of the detected vertical stopping positions of the sample or reagent dispensing probe.

11. The liquid dispensing method for use in an automatic analyzer according to claim 10, further comprising:

displaying a screen for selecting a measurement item, entering the correction amount with respect to the aspiration or discharge of the sample or reagent, and deriving a calculation expression for the correction amount.

12. The liquid dispensing method for use in an automatic analyzer according to claim 7, further comprising:

displaying a screen for selecting beforehand whether or not the correction amount, with respect to the aspiration or discharge of the sample or reagent, or to the measured data, is applied to analytical items to be measured.

13. The liquid dispensing method for use in an automatic analyzer according to claim 7, further comprising:

displaying a screen for selecting on an analytical item basis whether or not the correction, with respect to the aspiration or discharge of the sample or reagent, or to the measured data, is applied.

14. The automatic analyzer according to claim 2, further comprising:

a screen display;

wherein the controller is further programmed to display a screen for selecting whether or not a correction unit of the measurement data of the sample or reagent is applied to an analytical item to be measured.

15. The automatic analyzer according to claim 2, further comprising:

a screen display;

wherein the controller is further programmed to display a screen for selecting, for each of the analytical items, whether or not a correction amount of the measurement data is applied to an analytical item to be measured.

16. The liquid dispensing method for use in an automatic analyzer according to claim 8, further comprising the step of:

displaying a screen for previously selecting whether or not a correction amount of the measurement data of the sample or reagent is applied to an analytical item to be measured.

17. The liquid dispensing method for use in an automatic analyzer according to claim 8, further comprising the step of:

displaying a screen for selecting, for each of the analytical items, whether or not a correction amount of the measurement data is applied to an analytical item to be measured.

* * * * *